(12) United States Patent
Inagaki et al.

(10) Patent No.: US 7,655,121 B2
(45) Date of Patent: Feb. 2, 2010

(54) GAS SENSOR INTERFACE DEVICE AND GAS SENSOR SYSTEM

(75) Inventors: Hiroshi Inagaki, Aichi (JP); Tomonori Uemura, Aichi (JP); Norikazu Ieda, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 437 days.

(21) Appl. No.: 11/798,234

(22) Filed: May 11, 2007

(65) Prior Publication Data

US 2007/0272551 A1 Nov. 29, 2007

(30) Foreign Application Priority Data

May 23, 2006 (JP) ............................. 2006-143282

(51) Int. Cl.
*G01N 27/41* (2006.01)
(52) U.S. Cl. ..................... 204/406; 204/424; 204/425; 204/426; 204/427; 73/23.32; 123/694; 123/695; 123/696; 123/697
(58) Field of Classification Search ................ 204/406, 204/424–427; 73/23.32; 123/694–697
See application file for complete search history.

(56) References Cited

U.S. PATENT DOCUMENTS 6,164,125 A * 12/2000 Kawase et al. ............ 73/114.73

| 2002/0162743 | A1* | 11/2002 | Inagaki ...................... 204/425 |
| 2004/0089545 | A1 | 5/2004 | Kawase et al. |
| 2006/0219553 | A1* | 10/2006 | Ieda et al. .................... 204/424 |
| 2007/0056860 | A1* | 3/2007 | Inagaki et al. ............ 205/784.5 |
| 2007/0119437 | A1* | 5/2007 | Hiraiwa et al. .............. 123/693 |
| 2007/0273540 | A1* | 11/2007 | Inoue et al. ................. 340/632 |
| 2008/0060941 | A1* | 3/2008 | Ieda et al. .................... 204/431 |
| 2009/0095052 | A1* | 4/2009 | Inoue et al. ................ 73/23.32 |

FOREIGN PATENT DOCUMENTS

| JP | 1-152356 A | 6/1989 |
| JP | 2004-205488 A | 7/2004 |
| JP | 2005-326388 A | 11/2005 |

* cited by examiner

*Primary Examiner*—Bruce F Bell
(74) *Attorney, Agent, or Firm*—Sughrue Mion, PLLC

(57) ABSTRACT

An interface device for a gas sensor includes a detection resistor having first and second ends to generate voltages by a current output of the gas sensor, a differential amplifier having first and second input terminals to receive the voltages of the first and second resistor ends and an output terminal to output a voltage according to a difference between the voltages of the first and second resistor ends, a first switching element to transmit the voltage of the first resistor end to the first input terminal of the differential amplifier in a transmission state and interrupt transmission of the voltage of the first resistor end to the first input terminal of the differential amplifier in an interruption state and a second switching element turned on to establish continuity between the first and second input terminals of the differential amplifier when the first switching element is in the interruption state.

7 Claims, 4 Drawing Sheets

GAS SENSOR INTERFACE DEVICE AND GAS SENSOR SYSTEM

BACKGROUND OF THE INVENTION

The present invention relates to a gas sensor interface device for interfacing a gas sensor to external equipment and a gas sensor system equipped with the gas sensor interface device.

Under present circumstances where automotive emission regulations are becoming strict year after year, there is a demand to provide an internal combustion engine with a high-precision exhaust gas sensor and sensor control system for accurate engine air-fuel ratio control. In the case of a gasoline vehicle, the internal combustion engine commonly employs a three-way catalyst and, when operated in stoichiometric conditions, achieves maximum catalyst efficiency to clean deleterious exhaust gas highly efficiently. It is thus particularly desirable, as a low-emission control technique, to control an air-fuel ratio of the engine with no or less deviation from a stoichiometric air-fuel ratio value.

One example of the exhaust gas sensor is oxygen sensors. The oxygen sensors can be classified into two types: one type is a so-called "γ sensor" capable of producing a binary output according to the concentration of oxygen in exhaust gas, i.e., whether the air-fuel ratio is on the rich side or lean side of stoichiometry; and the other is a full-range sensor capable of producing an output with a certain degree of linearity over a wide oxygen concentration range. The full-range oxygen sensor enables more accurate engine air-fuel ratio control. The full-range oxygen sensor also enables not only stoichiometric combustion control (feedback control of the air-fuel ratio to around a stoichiometric value) but also lean combustion control (feedback control of the air-fuel ratio within a lean range) accurately.

The output of the full-range oxygen sensor is generally in the form of a current signal responsive to the concentration of oxygen in exhaust gas. As the current signal of the oxygen sensor is transmitted to any external equipment via a gas sensor interface device, a current detector is arranged in the first circuit stage of the gas sensor interface device to detect the current signal from the full-range oxygen sensor. Each of Japanese Laid-Open Patent Publication No. 1-152356 and No. 2004-205488 proposes such a current detector circuit for use in the gas sensor interface device, including a detection resistor and a differential amplifier to generate an output voltage by amplifying a potential difference across the detection resistor upon receipt of the current output from the oxygen sensor.

SUMMARY OF THE INVENTION

The differential amplifier unavoidably shows performance variations depending on its circuit component performance and temperature characteristics. For accurate engine air-fuel ratio control, it is conceivable to compensate for these performance variations by measuring an offset voltage of the differential amplifier and correcting the amplifier output voltage with the offset voltage. During the measurement of the offset voltage, however, the inverting and non-inverting input terminals of the differential amplifier has to be maintained at the same potential. If the exhaust gas sensor is once deactivated forcibly to interrupt the current output of the gas sensor to the detection resistor and thereby maintain the inverting and non-inverting input terminals of the differential amplifier at the same potential, it takes time to reactivate the exhaust gas sensor so that the resulting sensor activation delay may impair accurate engine air-fuel ratio control. For this reason, it is desired to develop a technique of compensating for the performance variations of the differential amplifier during the operation (activation) of the gas sensor without deactivating the gas sensor.

It is accordingly an object of the present invention to provide a gas sensor interface device capable of interfacing a gas sensor with external equipment so as to obtain an output of the gas sensor precisely responsive to the concentration of a specific gas component in measurement gas without the influence of interface circuit performance variations.

It is also an object of the present invention to provide a gas sensor system equipped with the gas sensor interface device.

According to one aspect of the present invention, there is provided an interface device for a gas sensor, the gas sensor being capable of producing a current output responsive to the concentration of a specific gas component in measurement gas, the interface device comprising: a detection resistor having first and second resistor ends through which the current output of the gas sensor flows to generate voltages of opposite polarity at the first and second resistor ends; a differential amplifier having first and second input terminals to receive the voltages of the first and second resistor ends, respectively, and an output terminal to output a voltage according to a difference between the voltages of the first and second resistor ends; a first switching element switched between a transmission state and an interruption state so as to transmit the voltage of the first resistor end to the first input terminal of the differential amplifier in the transmission state and interrupt transmission of the voltage of the first resistor end to the first input terminal of the differential amplifier in the interruption state; and a second switching element turned on to establish continuity between the first and second input terminals of the differential amplifier when the first switching element is in the interruption state.

According to another aspect of the present invention, there is provided a gas sensor system, comprising: a gas sensor having a sensing cell, a pumping cell and a measurement gas chamber defined between the sensing cell and the pumping cell so as to feed measurement gas into or out of the measurement gas chamber by the flow of an electric current through the pumping cell and output the electric current as a current output responsive to the concentration of a specific gas component in the measurement gas; and an interface device including: a detection resistor having first and second resistor ends through which the current output of the gas sensor flows to generate voltages of opposite polarity at the first and second resistor ends; a differential amplifier having first and second input terminals to receive the voltages of the first and second resistor ends, respectively, and an output terminal to output a voltage according to a difference between the voltages of the first and second resistor ends; a first switching element switched between a transmission state and an interruption state so as to transmit the voltage of the first resistor end to the first input terminal of the differential amplifier in the transmission state and interrupt transmission of the voltage of the first resistor end to the first input terminal of the differential amplifier in the interruption state; a second switching element turned on to establish continuity between the first and second input terminals of the differential amplifier when the first switching element is in the interruption state: and a current control circuit that controls the flow of the electric current through the pumping cell so as to maintain a voltage developed across the sensing cell at a predetermined level.

The other objects and features of the present invention will also become understood from the following description.

DESCRIPTION OF THE EMBODIMENTS

Figure 1:
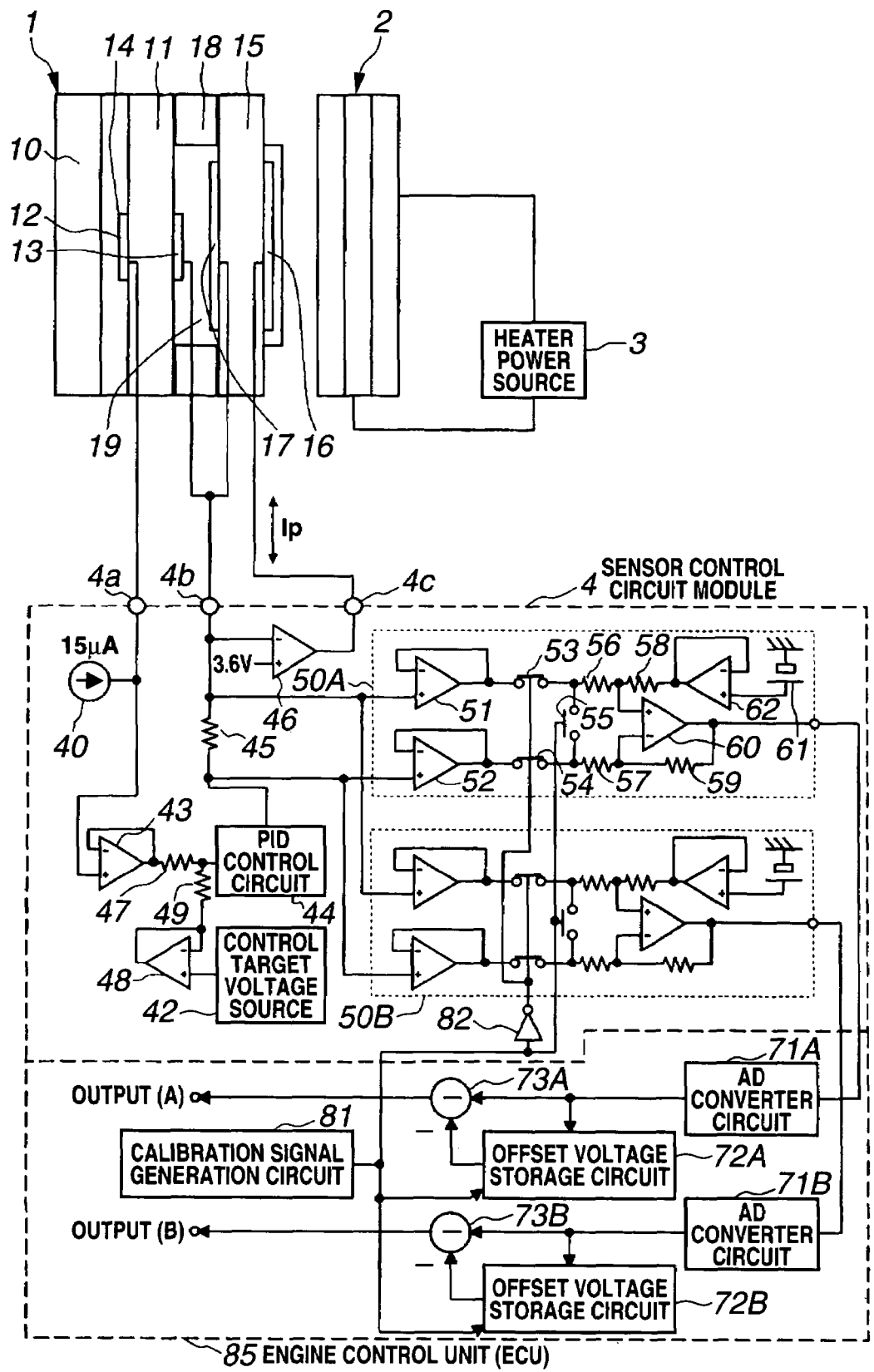
FIG. 1 is a circuit block diagram of a gas sensor system with a gas sensor and a sensor interface device according to one exemplary embodiment of the present invention.

The present invention will be described below by way of the following first to third embodiments in which like parts and portions are designated by like reference numerals.

The first embodiment of the present invention will be first explained below with reference to FIGS. 1 to 3.

Figure 2:
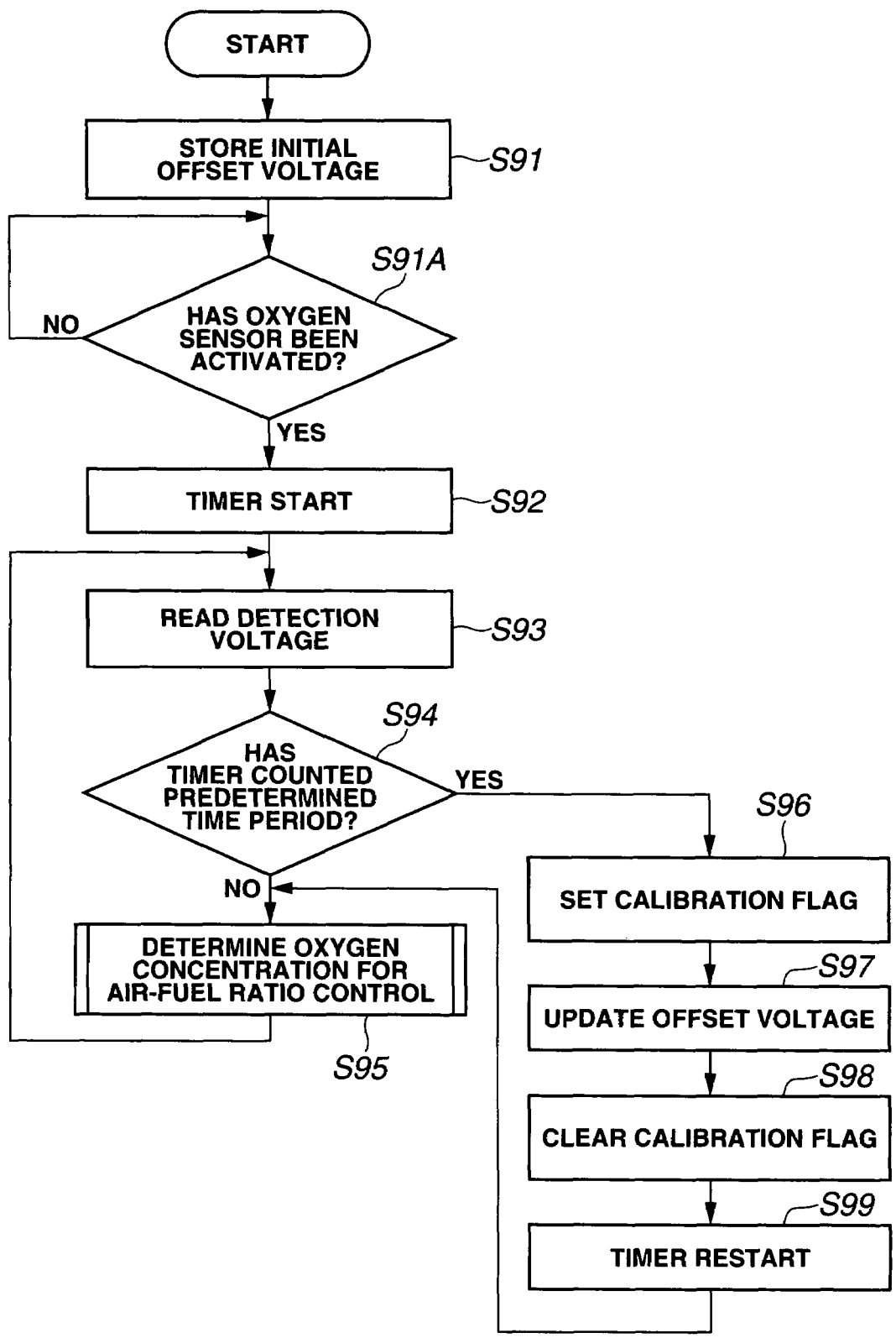
FIG. 2 is a flowchart for operation of the sensor interface device according to one exemplary embodiment of the present invention.

Referring to FIG. 1, a gas sensor system of the first embodiment is designed for use in an internal combustion engine e.g. gasoline engine and includes an oxygen sensor 1, a heater 2 with a power source 3, a sensor control circuit module 4 and an engine control unit (ECU) 85. The oxygen sensor 1 is a full-range oxygen sensor capable of outputting a current signal linearly responsive to the concentration of oxygen in engine exhaust gas (the air-fuel ratio of the engine). The heater 2 is located adjacent to the oxygen sensor 1 and energized with the power source 3 to activate the oxygen sensor 1 by heating. The sensor control circuit module 4 can be external or internal to the ECU 85 and configured to control the operations of the oxygen sensor 1 while processing and transmitting the output signal of the oxygen sensor 1 to the ECU 85 so that the ECU 85 performs engine air-fuel ratio feedback control by fuel supply regulation based on the output of the oxygen sensor 1. Namely, the sensor control circuit module 4 functions, together with a part of the ECU 85, a gas sensor interface device in the present embodiment.

More specifically, the oxygen sensor 1 has a shield plate 10, a solid electrolyte layer 11, a first pair of porous electrodes 12 and 13, a solid electrolyte 15, a second pair of porous electrodes 16 and 17 and a gas diffusion material 18 as shown in FIG. 1.

The solid electrolyte layer 11 is arranged on one side of the shield plate 10. The porous electrodes 12 and 13 are arranged on opposite sides of the solid electrolyte layer 11. The solid electrolyte layer 15 is arranged on the side of the solid electrolyte layer 11 opposite from the shield plate 10. The porous electrodes 16 and 17 are arranged on opposite sides of the solid electrolyte layer 15. These arrangements provide a reference gas chamber 14 defined between the shield plate 10 and the solid electrolyte layer 11 with the porous electrode 12 being exposed to the reference gas chamber 14 as well as a measurement gas chamber 19 defined between the solid electrolyte layers 11 and 15 with the porous electrodes 13 and 17 being exposed to the measurement gas chamber 19.

Each of the solid electrolyte layers 11 and 15 is made of an oxygen ion conductive material e.g. zirconia ($ZrO_2$) to show, when heated to an active state, the property of decreasing its internal impedance to allow oxygen ion conduction through the solid electrolyte layer 11, 15.

The gas diffusion material 18 is arranged between the solid electrolyte layers 11 and 15 so as to function as a partition between the measurement gas chamber 19 and the exhaust gas source (the outside of the oxygen sensor 1) while diffusing the exhaust gas into or out of the measurement gas chamber 19.

In the present embodiment, the solid electrolyte layer 11 and the porous electrodes 12 and 13 forms an electrochemical cell (hereinafter referred to as a "sensing cell"). When a weak electric current of e.g. 15 µA is passed through the sensing cell in a direction from one porous electrode 12 to the other porous electrode 13 during the active state of the solid electrolyte layer 11, the solid electrolyte layer 11 allows oxygen conduction from the measurement gas chamber 19 to the reference gas chamber 14 so as to accumulate some amount of oxygen as reference gas in the reference gas chamber 14. There arises a voltage as an electromotive force between the sensing cell electrodes 12 and 13 due to a difference in oxygen concentrations between the gas chambers 18 and 19. In view of the property of the solid electrolyte layer 11, the electromotive voltage of the sensing cell is about 450 mV when the oxygen concentration in the measurement gas chamber 19 is at a level equivalent to the stoichiometric air-fuel ratio in the present embodiment. As the oxygen concentration in the measurement gas chamber 19 deviates from the stoichiometric air-fuel ratio level, the electromotive voltage of the sensing cell becomes saturated to upper and lower voltages.

Further, the solid electrolyte layer 15 and the porous electrodes 16 and 17 form another electrochemical cell (hereinafter referred to as a "pumping cell") in the present embodiment. When an electric current Ip is passed between the porous electrodes 16 and 17 of the pumping cell during the active state of the solid electrolyte layer 15, the solid electrolyte layer 15 allows oxygen conduction from the exhaust gas source to the measurement gas chamber 19, or from the measurement gas chamber 19 to the exhaust gas source, depending on the direction of flow of the pumping cell current Ip.

On the other hand, the sensor control circuit module 4 is electrically connected at input/output terminals 4a, 4b and 4c with the oxygen sensor 1 and includes a sensing cell current source 40, a control target voltage source 42, a PID control circuit 44, operational amplification circuits 43 and 48, a detection resistor 45, an amplifier 46 and resistors 47 and 49 as shown in FIG. 1.

The sensing cell current source 40 supplies a weak electric current of e.g. 15 µA through the sensing cell of the oxygen sensor 1 for generation of the electromotive voltage between the sensing cell electrodes 12 and 13 as explained above. The output voltage (generation voltage) of the sensing cell is transmitted to the sensor control circuit module 4 through the terminal 4a, buffered by the operational amplification circuit 43, and then, inputted to the PID control circuit 44 via the resistor 47.

The control target voltage source 42 generates a control target voltage of e.g. 450 mV as a target value for control of the pumping cell current Ip. The control target voltage is buffered by the operational amplification circuit 48, and then, inputted to the PID control circuit 44 via the resistor 49.

The amplifier 46 has an inverting input terminal connected to the terminal 4b, a non-inverting input terminal connected to a reference voltage of e.g. 3.6 V and an output terminal connected to the terminal 4c, so as to flow the pumping cell current Ip while maintaining the voltage of the terminal 4b at the reference voltage (as artificial ground).

The PID control circuit 44 has an input terminal connected to the terminal 4a through the operational amplification circuit 43 and the resistor 47 and to the control target voltage source 42 through the operational amplification circuit 48 and the resistor 49 and an output terminal connected to the inverting input terminal of the amplifier 46 through the detection resistor 45. In the present embodiment, the PD control circuit 44 forms, together with the amplifier 46, a current feedback circuit configuration to calculate a difference ΔVs between the sensing cell output voltage and the control target voltage and determine the amount and direction of flow of the pumping cell current Ip according to the voltage difference ΔVs.

The amount and direction of flow of the pumping cell current Ip is determined in such a manner that the electromotive voltage of the sensing cell is maintained at a predetermined level, i.e., the oxygen concentration in the measurement gas chamber 19 becomes equivalent to the stoichiometric air-fuel ratio level. The pumping cell current Ip is zero without the necessity for oxygen conduction through the solid electrolyte layer 15 when the oxygen concentration in the exhaust gas source is equivalent to the stoichiometric air-fuel ratio level. When the oxygen concentration in the exhaust gas source is not equivalent to the stoichiometric air-fuel ratio level, the pumping cell current Ip flows from or to the pumping cell through the detection resistor 45 depending on the degree of deviation from the stoichiometric air-fuel ratio level. In this way, the amount and direction of flow of the pumping cell current Ip changes with the oxygen concentration in the exhaust gas source. The oxygen concentration of the exhaust gas can be thus determined upon detection of the pumping cell current Ip through the detection resistor 45. This allows oxygen concentration measurements over a wide concentration range.

The sensor control circuit module 4 also includes detection circuits 50A and 50B arranged to form a two-channel detection circuit configuration for detection of the pumping cell current Ip through the detection resistor 45 as shown in FIG. 1.

The detection circuit 50A consists of operational amplifiers 51 and 52 (voltage followers), switches 53 and 54 (as first and third or third and first switching elements), a switch 55 (as a second switching element), an operational amplifier 60, resistors 56 to 59, a reference voltage source 61 and an operational amplifier 62.

As explained above, the detection resistor 45 is connected in series between the output terminal of the PID control circuit 44 and the inverting input terminal of the amplifier 46 and has two opposite ends through which the pumping cell current Ip flows to generate voltages of opposite polarity at the respective resistor ends.

The operational amplifiers 51 and 52 are connected with the opposite ends of the detection resistor 45 so as to buffer and output the voltages of the opposite ends of the detection resistor 45 to the switches 53 and 54, respectively.

The switches 53 and 54 are turned on under normal conditions i.e. during operation (activation) of the oxygen sensor 1 so as to allow transmission of the output voltages of the detection resistor 45 to the next circuit stage. By contrast, the switches 53 and 54 are turned off during calibration so as to interrupt transmission of the output voltages of the detection resistor 45. The switch 55 is turned off under normal conditions and turned on during calibration, thereby switching the detection circuit 50A between a detection state and a calibration state as will be explained later. Each of the switches 53, 54 and 55 can be formed of e.g. a semiconductor element.

The operational amplifier 60 functions together with the resistors 56 to 59, as a differential amplifier using ends of the resistors 56 and 57 as input terminals. One of the output voltages of the detection resistor 45 is amplified by the resistors 56 and 58 with a first amplification factor, whereas the other of the output voltages of the detection resistor 45 is amplified by the resistors 57 and 59 with a second amplification factor. The first and second amplification factors can be determined by dividing the resistance value of the resistor 58 by the resistance value of the resistor 56 and dividing the resistance value of the resistor 59 by the resistance value of the resistor 57, respectively. In general, the first and second amplification factors are set at the same degree. The operational amplifier 60 receives a reference voltage defined by the reference voltage source 61 and the operational amplifier 62 and outputs a voltage proportional to a difference between the above amplified resistor voltages. The output voltage of the detection circuit 50A with respect to the reference voltage is given as an output signal of the detection circuit 50A precisely responsive to the pumping cell current Ip. The reference voltage and the amplification factors of the differential amplifier can be set as appropriate according to how the output signal of the detection circuit 50A is processed in the subsequent processing operation.

The detection circuit 50B is substantially similar in structure to the detection circuit 50A except for the detail circuit design specifications, whereby an explanation of the configuration of the detection circuit 50B will be omitted for the sake of simplicity.

In the present embodiment, the overall amplification factors a and b of the detection circuits 50A and 50B are set at different values in such a manner as to satisfy a relationship of a<b. The amplification factor a of the detection circuit 50A is set corresponding to a full oxygen concentration detection range; and the amplification factor b of the detection circuit 50B is set corresponding to a narrow (specific) oxygen concentration detection range at around the stoichiometric air-fuel ratio level.

The ECU 85 includes AD converter circuits 71A and 71B, as shown in FIG. 1, to convert the output signals of the detection circuits 50A and 50B into digital signals and determine the exhaust oxygen concentration upon selection of appropriate one of these digital signals for engine air-fuel ratio feedback control.

Herein, the performance of the detection circuit 50A, 50B may vary depending on the performance and temperature characteristics of the circuit components 51 to 62, notably the differential amplifier 60.

In order to calibrate the detection circuits 50A and 50B and compensate for the performance variations of the detection circuits 50A and 50B, the sensor control circuit module 4 includes an inverter 82; and the ECU 85 includes offset voltage storage circuits 72A and 72B, subtraction circuits 73A and 73B and a calibration signal generation circuit 81 as shown in FIG. 1.

The calibration signal generator 81 generates a calibration signal at regular time intervals for on-off control of the switches 53 to 55. Alternatively, the calibration signal may be generated in appropriate timing, e.g., during fuel cut.

The inverter 82 processes and transmits the calibration signal to each of the switches 53 to 55 of the detection circuit 50A, 50B in such a manner that the calibration signal to the switches 53 and 54 is inverted to the calibration signal to the switch 55.

When the calibration signal to the switch 55 is active, the switch 55 is turned to the ON position and the switches 53 and 54 are turned to the OFF position. In this state, the impedance of the circuit stage (including the detection resistor 45) upstream of the differential amplifier of the detection circuit 50A, 50B becomes high so as to interrupt electrical connection between the detection resistor 45 and the differential amplifier of the detection circuit 50A, 50B and thereby prevent transmission of the output voltages of the detection resistor 45 to the differential amplifier of the detection circuit 50A, 50B. Concurrently, the switch 55 provides continuity between the input terminals of the differential amplifier of the detection circuit 50A, 50B. The differential amplifier of the detection circuit 50A, 50B thus generates an offset voltage irrespective of the output Ip of the oxygen sensor 1. The offset voltage is digitized by the AC converter circuit 71A, 71B and stored in the offset voltage storage circuit 72A, 72B.

When the calibration signal to the switch 55 is inactive, the switches 53 and 54 are turned to the ON position and the switch 55 is turned to the OFF position. The output voltages of the detection resistor 45 are then transmitted to and processed by the differential amplifier of the detection circuit 50A, 50B. The subtraction circuit 73A, 73B retrieves the offset voltage from the offset voltage storage circuit 72A, 72B, receives the output voltage of the detection circuit 50A, 50B and subtracts the output voltage of the detection circuit 50A, 50B by the offset voltage. The thus-calibrated output voltage of the detection circuit 50A, 50B is in precise agreement with the pumping cell current Ip, i.e., the oxygen concentration of the exhaust gas.

By the electrical disconnection of the detection resistor 45 to the differential amplifier of the detection circuit 50A, 50B during the calibration, the offset voltage can be detected without the influence of the pumping cell current Ip even when the pumping cell current Ip flows through the detection resistor 45. There is no need to stop the flow of the pumping cell current Ip through the detection resistor 45 and deactivate the oxygen sensor 1 forcibly during the calibration. It is therefore possible to perform calibration (offset voltage correction) of the detection circuit 50A, 50B during the activation of the oxygen sensor 1. In addition, the calibration (offset correction) can be performed periodically by outputting the calibration signal at the regular intervals. Even if the performance of the detection circuit 50A, 50B varies in response to changes in environmental conditions (e.g. temperature), it is possible to compensate for such performance variations by the periodical calibration process.

Although not specifically shown in the drawings, the sensor control circuit module 4 includes any other necessary circuit components such as an impedance detection circuit to detect an internal impedance of the sensing cell of the oxygen sensor 1. Furthermore, the ECU 85 can employ any known type of circuit configuration for control of the air-fuel ratio whereby an explanation of the air-fuel ratio control configuration of the ECU 85 will be omitted for the sake of simplicity.

The above-structured gas sensor system operates as follows according to a software program shown in FIG. 2.

At step S91, the gas sensor system allows the offset voltage storage circuit 72A, 72B to store an initial offset voltage value. The initial offset voltage can be determined as e.g. the setting voltage of the reference voltage generator 61 of the detection circuit 50A, 50B. The program control then proceeds to step S91A.

At step S91A, the gas sensor system judges whether the oxygen sensor 1 has been activated based on a signal from the sensing cell impedance detection circuit of the sensor control circuit module 4. If No at step S91A, the control repeats this step until the oxygen sensor 1 is judged as being activated. If Yes at step S91A, the control goes to step S92.

At step S92, the gas sensor system starts a timer. The program control proceeds to step S93.

At step S93, the gas sensor system leads the output of the detection circuit 50A, 50B to the subtraction circuit 73A, 73B. The program control then proceeds to step S94.

At step S94, the gas sensor system judges whether the timer has counted a predetermined time period. This time period can be set to e.g. about 5 seconds depending on the frequency with which the calibration (offset voltage correction) is performed. If No at step S94, the control goes to step S95 for oxygen concentration detection. If Yes at step S94, the control goes through steps 96 to 99 for calibration.

At step S95, the gas sensor system allows the subtraction circuit 73A, 73B to read the output voltage of the detection circuit 50A, 50B, retrieve the offset voltage from the offset voltage storage circuit 72A, 72B and subtract the output voltage of the detection circuit 50A, 50B by the offset voltage so that the ECU 85 determines the oxygen concentration of the exhaust gas using either one of the outputs of the subtraction circuits 73A and 73B and performs air-fuel ratio feedback control according to the oxygen concentration of the exhaust gas. After that, the control goes back to step S93.

At step S96, the gas sensor system sets a calibration flag. With this, the calibration signal becomes active so that the detection circuit 50A, 50B shifts to the calibration state. The program control then proceeds to step S97.

At step 97, the gas sensor system allows the offset voltage storage circuit 72A, 72B to update and store the offset voltage of the differential amplifier of the detection circuit 50A, 50B. The program control proceeds to step S98.

At step S98, the gas sensor system clears the calibration flag to return the detection circuit 50A, 50B to normal operation conditions. The program control proceeds to step S99.

At step S99, the gas sensor system restarts the timer. The control then goes back to step S95.

Accordingly, the gas sensor system is capable of detecting the oxygen concentration of the exhaust gas with high precision, for accurate air-fuel ratio control, without the influence of the circuit performance variations.

Although two switches 53 and 54 are provided in the detection circuit 50A, 50B and operated in synchronism with each other in the present embodiment, only one of the switches 53 and 54 may alternatively be provided in the detection circuit 50A, 50B to selectively allow and interrupt transmission of the output voltages of the detection resistor 45 to the differential amplifier of the detection circuit 50A, 50B. Even with the use of only one of the switches 53 and 54, both of the input terminals of the differential amplifier of the detection circuit 50A, 50B can be maintained at the same voltage for generation of the offset voltage. However, the differential amplifier of the detection circuit 50A, 50B would be capable of more precise offset voltage output through the use of two switches 53 and 54 for improvement of the interface functionality of the sensor control circuit module 4.

In order to lead the output voltages of the detection resistor 45 to the detection circuit 50A, 50B without the influence on the flow of the pumping cell current Ip through the detection resistor 45 and thereby improve the electrical ruggedness of the sensor control circuit module 4, the operational amplifiers 51 and 52 are used as buffers (voltage followers) in the first circuit stage of the detection circuit 50A, 50B as explained above.

Figure 3:
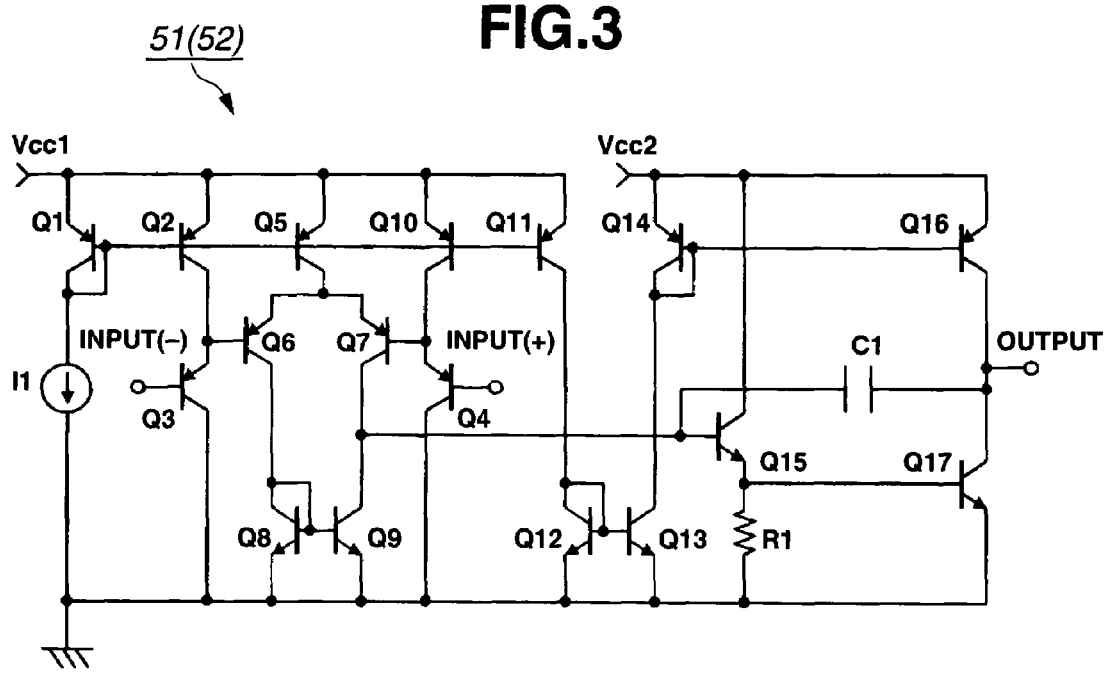
FIG. 3 is a circuit diagram of an operational amplifier of the sensor interface device according to one exemplary embodiment of the present invention.

The operational amplifiers 51 and 52 may be formed with an ingenious circuit configuration as shown in FIG. 3. In FIG. 3, the terms "input (+)", "input (−)" and "output" designate a non-inverting input terminal, an inverting input terminal and an output terminal, respectively.

As shown in FIG. 3, the operational amplifier 51, 52 has input and output stages formed with separate power supply voltage terminals so that different power supply voltages Vcc1 and Vcc2 are applied to the input and output stages of the operational amplifier 51, 52 through the respective power supply voltage terminals for prevention of excessive voltage output from the operational amplifier 51, 52 to the switch 55 via the switch 53, 54. In the present embodiment, the output-stage power supply voltage Vcc2 is set lower than the input-stage power supply voltage Vcc1.

More specifically, each of the operational amplifiers 51 and 52 consists of a current source I1, transistors Q1 to Q17, a resistor R1 and a capacitor C1. The current source I1 and the transistors Q1, Q2, Q5, Q10 and Q11 form a current mirror so that the transistors Q2, Q5, Q10 and Q11 output collector currents therethrough to ground. The transistors Q12 and Q13 form a current mirror driven by the current output of the transistor Q11. The transistors Q14 and 16 also form a current mirror driven by the current output of the transistor Q1. In these circuit arrangements, the transistor Q16 serves as a load on the transistor Q17. The transistors Q3 and Q4 act as emitter-followers to buffer the inverting and non-inverting inputs of the operational amplifier 51, 52, respectively. The transistors Q6 and Q7 form a differential pair supplied with the buffered inverting and non-inverting inputs to provide collector currents to the transistors Q8 and Q9. The transistors Q8 and Q9 form a current mirror and serve as a load on the differential pair of the transistors Q6 and Q7 so that the current output of the differential pair is produced from the connection node between the collectors of the transistor Q7 and Q9. The transistor Q15 increases and decreases its base current according to the current output of the differential pair.

In the case where the non-inverting input is lower than the inverting input, the current output of the differential transistor pair is produced in a positive direction so that the transistor Q15 provides an emitter current hFE times larger than the base current. At this time, the current through the resistor R1 is kept substantially constant when the transistor Q17 is ON. As the transistor Q17 increases its base current according to the emitter current of the transistor Q15, the collector voltage of the transistor Q17 becomes decreased under the load of the transistor Q16.

By contrast, the current output of the differential transistor pair is not produced in a positive direction to provide the transistor Q15 with no base current in the case where the non-inverting input is higher than the inverting input. The transistors Q15 and Q17 are then cut off. The collector voltage of the transistor Q16 becomes increased under the load of the transistor Q17.

As a result, the operational amplifier 51, 52 produces a voltage output from the output terminal (i.e. the connection node between the collectors of the transistors Q16 and Q17), with a large gain, in response to a voltage difference between the inverting and non-inverting input terminals. The capacitor C1 is arranged between the base of the transistor Q15 and the connection node between the, collectors of the transistors Q16 and Q17 for phase compensation.

With the above circuit configuration, the operational amplifier 51, 52 has its input and output stages operated at different power supply voltages Vcc1 and Vcc2 (Vcc1>Vcc2) and makes a feedback connection between the inverting input terminal and the output terminal to establish a so-called imaginary short of the inverting and non-inverting input terminals and maintain the inverting and non-inverting input terminals at the same potential. The output voltage of the operational amplifier 51, 52 can be thus limited to the power supply voltage Vcc2 or lower. By this output voltage limiting function, the operational amplifier 51, 52 is able to prevent unexpected excessive voltage from being applied to the switch 55 through the operational amplifier (buffer) 51, 52 and the switch 53, 54 in the event that a voltage malfunction occurs in one end of the detection resistor 45 e.g. the terminal 4b of the sensor control circuit module 4 is short-circuited to battery voltage. Even in the event of such an electrical malfunction, it is possible to limit the voltage across the switch 55 to the withstand voltage of the switch 55 or lower and protect the switch 55 from breakage or failure. The operational amplifier 51, 52 with the output voltage limiting function is suitable particularly when the switch 55 is formed of a MOS (Metal Oxide Semiconductor) element having a withstand voltage of about 10 V. It is desirable to provide the output voltage limiting function to at least the operational amplifier 51 adjacent to the terminal 4b of the sensor control circuit module 4.

Figure 4:
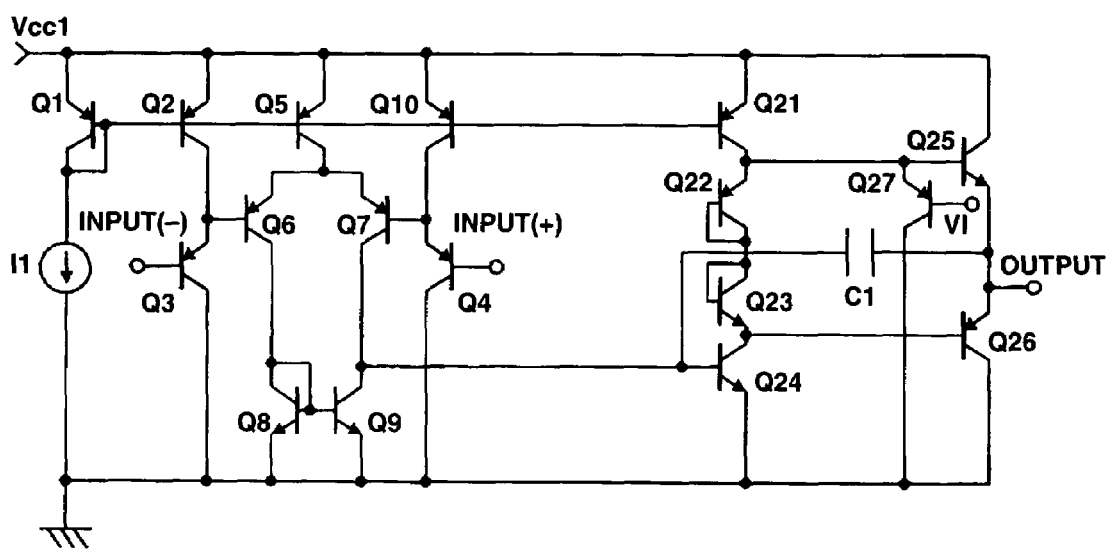
FIG. 4 is a circuit diagram of an operational amplifier of the sensor interface device according to another exemplary embodiment of the present invention.

The second embodiment will be next explained below with reference to FIG. 4. A gas sensor system of the second embodiment is structurally similar to that of the first embodiment, except that at least one of the detection circuits 50A and 50B utilizes an operational amplifier 51A in place of the operational amplifier 51, 52 as shown in FIG. 4. In FIG. 4, the terms "input (+)", "input (−)" and "output" designate a non-inverting input terminal, an inverting input terminal and an output terminal, respectively. The operational amplifier 51A is also used as a buffer (voltage follower) in order to lead the output voltages of the detection resistor 45 to the detection circuit 50A, 50B without the influence on the flow of the pumping cell current Ip through the detection resistor 45 and improve the electrical ruggedness of the sensor control circuit module 4.

As shown in FIG. 4, the operational amplifier 51A has a voltage limiter in its output stage for prevention of excessive voltage output from the operational amplifier 51A to the switch 55 via the switch 53, 54. More specifically, the operational amplifier 51A consists of a current source I1, transistors Q1 to Q1 and Q21 to Q27 and a capacitor C1. Of these, the circuit components designated by the same reference numerals as in the first embodiment have the same functions. A detailed explanation of those circuit components will be omitted for the sake of simplicity. The transistor Q21 is incorporated in the current mirror of the current source 11 and the transistors Q1, Q2, Q5 and Q10 to output a collector current therethrough to ground via the transistors Q22 to Q24 so that the transistor Q21 serves as a load on the transistor Q24. Further, the transistors Q25 and 26 act as output buffers.

When the current output of the differential pair of the transistors Q6 and Q7 is produced from the connection node between the collectors of the transistor Q7 and Q9, the transistor Q24 increases and decreases its base current according to the current output of the differential pair. In the case where the non-inverting input is lower than the inverting input, the current output of the differential transistor pair is produced in a positive direction so that the transistor Q24 provides an emitter current hFE times larger than the base current. The collector voltage of the transistor Q24 becomes decreased under the load of the transistor Q21. By contrast, the current output of the differential transistor pair is not produced in a positive direction to provide the transistor Q24 with no base current in the case where the non-inverting input is higher than the inverting input. The transistor Q24 is cut off. The collector voltage of the transistor Q21 becomes increased under the load of the transistor Q24. Accordingly, the operational amplifier 51A produces a voltage output from the output terminal (i.e. the connection node between the emitters of the transistors Q25 and Q26), with a large gain, in response to a voltage difference between the inverting and non-inverting input terminals. The capacitor C1 is arranged between the base of the transistor Q24 and the connection node between the emitters of the transistors Q25 and Q26 for phase compensation.

It is now assumed that the voltage of the connection node between the emitters of the transistors Q25 and Q26 is increased and about to become higher than the base voltage of the transistor Q27 (V1=limit voltage). At this time, as the transistor Q27 is turned on, the base voltage of the transistor Q25 cannot become higher than V1+Vbe (Vbe=base-emitter voltage). The transistor Q25 is then cut off so that the upper limit voltage of the connection node between the emitters of the transistors Q25 and Q26 is approximately V1. Namely, the transistor Q27 acts as the voltage limiter that limits the output voltage of the operational amplifier 51A to approximately V1 or lower. By means of this voltage limiter, the operational amplifier 51A is able to prevent unexpected excessive voltage from being applied to the switch 55 through the operational amplifier 51A and the switch 53, 54 in the event that a voltage malfunction occurs in one end of the detection resistor 45 e.g. the terminal 4b of the sensor control circuit module 4 is short-circuited to battery voltage. Even in the event of such an electrical malfunction, it is possible to limit the voltage across the switch 55 to the withstand voltage of the switch 55 or lower and protect the switch 55 from breakage or failure.

Figure 5:
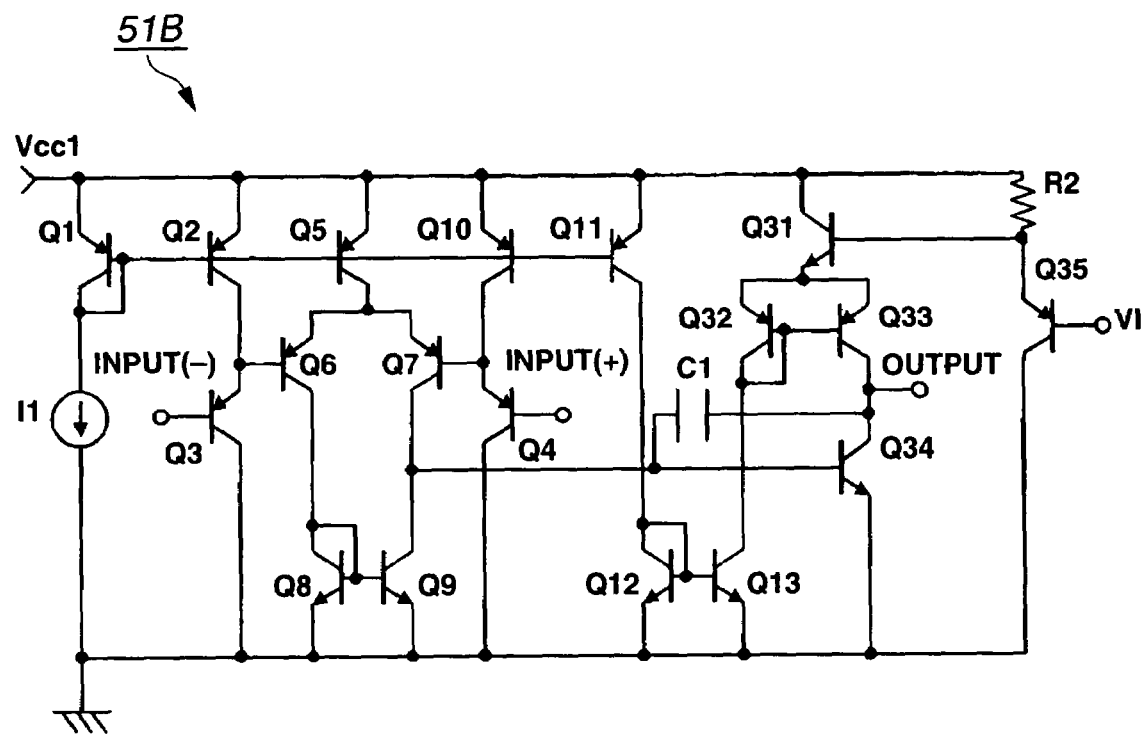
FIG. 5 is a circuit diagram of an operational amplifier of the sensor interface device according to still another exemplary embodiment of the present invention.

Finally, the third embodiment will be explained below with reference to FIG. 5. A gas sensor system of the third embodiment is structurally similar to that of the first and second embodiments, except that at least one of the detection circuits 50A and 50B utilizes an operational amplifiers 51B in place of the amplifier 51, 52, 51A as shown in FIG. 5. In FIG. 5, the terms "input (+)", "input (−)" and "output" designate a non-inverting input terminal, an inverting input terminal and an output terminal, respectively. The operational amplifier 51B is also used as a buffer (voltage follower) in order to lead the output voltages of the detection resistor 45 to the detection circuit 50A, 50B without the influence on the flow of the pumping cell current Ip through the detection resistor 45 and improve the electrical ruggedness of the sensor control circuit module 4.

As shown in FIG. 5, the operational amplifier 51B has a voltage limiter in its output stage for prevention of excessive voltage output from the operational amplifier 5B to the switch 55 via the switch 53, 54. More specifically, the operational amplifier 51B consists of a current source I1, transistors Q1 to Q13 and Q31 to Q35, a capacitor C1 and a resistor R2. Of these, the circuit components designated by the same reference numerals as in the first embodiment have the same functions. A detailed explanation of those circuit components will be omitted for the sake of simplicity. The transistors Q32 and Q33 forms a current mirror connected to the collector of the transistor Q13. Through the application of the limit voltage V1 to the base of the transistor Q35, the emitter voltage of the transistor Q35 becomes equal to V1+Vbe so that the transistor Q31 provides an emitter voltage of V1. As both of the emitters of the transistors Q32 and Q33 are connected to the emitter of the transistor Q31, the emitter voltage of the transistor Q32, Q33 is lowered from the power supply voltage Vcc1 to the limit voltage V1.

When the current output of the differential pair of the transistors Q6 and Q7 is produced from the connection node between the collectors of the transistor Q7 and Q9, the transistor Q34 increases and decreases its base current according to the current output of the differential pair. In the case where the non-inverting input is lower than the inverting input, the current output of the differential transistor pair is produced in a positive direction so that the transistor Q34 provides an emitter current hFE times larger than the base current. The collector voltage of the transistor Q34 becomes decreased under the load of the transistor Q33. By contrast, the current output of the differential transistor pair is not produced in a positive direction to provide the transistor Q34 with no base current in the case where the non-inverting input is higher than the inverting input. The transistor Q34 is cut off. The collector voltage of the transistor Q33 becomes increased under the load of the transistor Q34. Accordingly, the operational amplifier 51B produces a voltage output from the output terminal (i.e. the connection node between the emitters of the transistors Q33 and Q34), with a large gain, in response to a voltage difference between the inverting and non-inverting input terminals. The capacitor C1 is arranged between the base of the transistor Q34 and the connection node between the emitters of the transistors Q33 and Q34 for phase compensation.

In the operational amplifier 51B, the transistors Q31 and Q35 and the resistor R2 acts as the voltage limiter that limits the output voltage of the operational amplifier 51B to approximately V1 or lower as explained above. The operational amplifier 51B is thus able to prevent unexpected excessive voltage from being applied to the switch 55 through the operational amplifier 51B and the switch 53, 54 in the event that a voltage malfunction occurs in one end of the detection resistor 45 e.g. the terminal 4b of the sensor control circuit module 4 is short-circuited to battery voltage. Even in the event of such an electrical malfunction, it is possible to limit the voltage across the switch 55 to the withstand voltage of the switch 55 or lower and protect the switch 55 from breakage or failure.

Although the input and output stages of the operational amplifier 51, 52 are operated at different power supply voltages Vcc1 and Vcc2 in the first embodiment, the operational amplifier 51A, 51B is not divided into two separately operable input and output stages in the second and third embodiments. The lower power supply voltage Vcc2 is usually generated by stepping down the battery voltage. There is however a case that the battery current capacity is not so large in the actual applications. Even in such a case, the operational amplifier 51A, 51B can be configured, irrespective of the current capacity, with no need to generate the power supply voltage Vcc2.

The entire contents of Japanese Patent Application No. 2005-151247 (filed on May 24, 2005) and No. 2006-143282 (filed on May 23, 2006) are herein incorporated by reference.

Although the present invention has been described with reference to the above-specific embodiments of the invention, the invention is not limited to the these exemplary embodiments. Various modification and variation of the embodiments described above will occur to those skilled in the art in light of the above teaching. For example, the gas sensor system can utilize any other type of gas sensor such a limiting-current type gas sensor with a single cell or a gas sensor with three or more cells (including pumping cell) although the oxygen sensor 1 of two-cell type is used in the above embodiments. The scope of the invention is defined with reference to the following claims.

What is claimed is:

1. An interface device for a gas sensor, the gas sensor being capable of producing a current output responsive to the concentration of a specific gas component in measurement gas, the interface device comprising:
   a detection resistor having first and second resistor ends through which the current output of the gas sensor flows to generate voltages of opposite polarity at the first and second resistor ends;

a differential amplifier having first and second input terminals to receive the voltages of the first and second resistor ends, respectively, and an output terminal to output a voltage according to a difference between the voltages of the first and second resistor ends;

a first switching element switched between a transmission state and an interruption state so as to transmit the voltage of the first resistor end to the first input terminal of the differential amplifier in the transmission state and interrupt transmission of the voltage of the first resistor end to the first input terminal of the differential amplifier in the interruption state; and a second switching element turned on to establish continuity between the first and second input terminals of the differential amplifier when the first switching element is in the interruption state.

2. An interface device according to claim 1, the second switching element being turned off to interrupt the continuity between the first and second input terminals of the differential amplifier when the first switching element is in the transmission state; and the interface device further comprising:

an offset voltage storage circuit that stores as an offset voltage the output voltage of the differential amplifier when the first switching element is in the interruption state and the second switching element is turned on; and a subtraction circuit that subtracts the output voltage of the differential amplifier by the offset voltage when the first switching element is in the transmission state and the second switching element is turned off.

3. An interface device according to claim 1, further comprising:

a third switching element switched between a transmission state and an interruption state in synchronism with the first switching element so as to transmit the voltage of the second resistor end to the second input terminal of the differential amplifier in the transmission state and interrupt transmission of the voltage of the second resistor end to the second input terminal of the differential amplifier in the interruption state.

4. An interface device according to claim 1, further comprising a calibration signal generation circuit that generates a calibration signal periodically to switch the first switching element to the transmission state and turn on the second switching element.

5. An interface device according to claim 1, further comprising a buffer connected in series between the first resistor end of the detection resistor and the first input terminal of the differential amplifier and provided with an operational amplifier configuration as a voltage follower, the buffer having input and output stages formed with separate power supply voltage terminals and operated with the application of power supply voltages through the respective power supply voltage terminals.

6. An interface device according to claim 1, further comprising a buffer connected in series between the first resistor end of the detection resistor and the first input terminal of the differential amplifier and provided with an operational amplifier configuration as a voltage follower, the buffer having an input stage and an output stage formed with a voltage limiter to limit an output voltage of the buffer to a predetermined level or lower.

7. A gas sensor system, comprising:

a gas sensor having a sensing cell, a pumping cell and a measurement gas chamber defined between the sensing cell and the pumping cell so as to feed measurement gas into or out of the measurement gas chamber by the flow of an electric current through the pumping cell and output the electric current as a current output responsive to the concentration of a specific gas component in the measurement gas; and an interface device including:

a detection resistor having first and second resistor ends through which the current output of the gas sensor flows to generate voltages of opposite polarity at the first and second resistor ends;

a differential amplifier having first and second input terminals to receive the voltages of the first and second resistor ends, respectively, and an output terminal to output a voltage according to a difference between the voltages of the first and second resistor ends;

a first switching element switched between a transmission state and an interruption state so as to transmit the voltage of the first resistor end to the first input terminal of the differential amplifier in the transmission state and interrupt transmission of the voltage of the first resistor end to the first input terminal of the differential amplifier in the interruption state;

a second switching element turned on to establish continuity between the first and second input terminals of the differential amplifier when the first switching element is in the interruption state; and a current control module that controls the flow of the electric current through the pumping cell so as to maintain a voltage developed across the sensing cell at a predetermined level.

* * * * *